(12) United States Patent
Singh

(10) Patent No.: US 7,887,324 B2
(45) Date of Patent: Feb. 15, 2011

(54) OSTEOGENETIC-ORTHODONTIC DEVICE, SYSTEM, AND METHOD

(76) Inventor: Gurdev Dave Singh, 13538 NW. Kollenborn Ln, Portland, OR (US) 97229-4593

( * ) Notice: Subject to any disclaimer, the term of this patent is extended or adjusted under 35 U.S.C. 154(b) by 309 days.

(21) Appl. No.: 12/240,144

(22) Filed: Sep. 29, 2008

(65) Prior Publication Data

US 2009/0087810 A1 Apr. 2, 2009

Related U.S. Application Data

(60) Provisional application No. 60/976,425, filed on Sep. 29, 2007, provisional application No. 60/976,423, filed on Sep. 29, 2007.

(51) Int. Cl.
*A61C 7/00* (2006.01)
(52) U.S. Cl. .............................. 433/7; 433/24
(58) Field of Classification Search ...................... 433/7, 433/18, 19, 21, 24
See application file for complete search history.

(56) References Cited

U.S. PATENT DOCUMENTS

| | | | |
|---|---|---|---|
| 4,026,023 A * | 5/1977 | Fisher | 433/7 |
| 4,197,643 A * | 4/1980 | Burstone et al. | 433/20 |
| 6,604,943 B2 * | 8/2003 | White | 433/21 |
| 7,314,372 B2 | 1/2008 | Belfor et al. | |
| 7,357,635 B2 | 4/2008 | Belfor et al. | |
| 2005/0260534 A1* | 11/2005 | Belfor et al. | 433/24 |
| 2007/0264605 A1 | 11/2007 | Belfor et al. | |

\* cited by examiner

*Primary Examiner*—Ralph A Lewis
(74) *Attorney, Agent, or Firm*—Peter A. Haas, Esquire LLC

(57) ABSTRACT

In a preferred embodiment of the present invention, an osteo-genetic-orthodontic appliance, device, system, and method optimizes craniofacial homeostasis by means of a 3-D axial spring that influences the patient's genome and thereby addresses problems existing primarily within the mid-facial region, as well as the other contiguous regions. Growth and development of the craniofacial structures can be influenced by foundational (skeleto-dental) correction in concert with functional (myo-spatial) correction, according to the genome of a particular patient by means of the method and systems of the present invention.

19 Claims, 10 Drawing Sheets

FIG. 12
FIG. 13
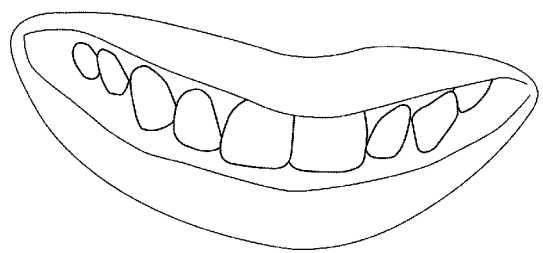
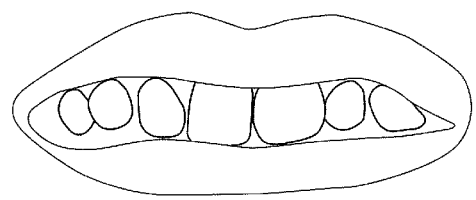

OSTEOGENETIC-ORTHODONTIC DEVICE, SYSTEM, AND METHOD

PRIORITY CLAIM

The present application claims benefit under 35 USC Section 119(e) of U.S. Provisional Patent Application Ser. No. 60/976,423 filed on 29 Sep. 2007 and of U.S. Provisional Patent Application Ser. No. 60/976,425 filed on 29 Sep. 2007. The present application is based on and claims priority from these applications, the disclosures of which are hereby expressly incorporated herein by reference.

BACKGROUND

The present invention relates to devices, systems, and treatment methods directed at aligning and correcting orthodontic or dentofacial abnormalities, including both foundational correction (a treatment that changes the skeletal and/or dental tissues) and functional correction (a treatment that changes the soft tissues and/or tissue spaces).

More specifically, the present invention relates to devices, systems, and methods incorporating osteogenetic-orthodontic appliances. Osteogenetic-orthodontic appliances are specialized orthopedic and/or orthodontic appliances that signal the genome of the patient to remodel tissues and spaces.

In contrast, the prior art teaches that common orthodontic and dentofacial abnormalities are suitably corrected by using treatment methods and devices that apply continuous forces via brackets and wires (which translate to vectors that apply force to teeth).

Traditional orthodontic or dentofacial treatments that address orthopedic correction are known as Phase I treatments and are characterized, typically, as using bio-mechanical systems. Examples known in the art include Twin Block appliances. After Phase I treatments for orthopedic correction, using brackets bonded to teeth, Phase II is undertaken: Correcting, leveling, aligning, and rotation of the teeth is undertaken using wires of various shapes and sizes.

The present invention, along with traditional methods and devices, attempts to correct common orthodontic and craniofacial abnormalities, which are undesired for both esthetic and medical reasons. For example, in the craniofacial region, a well-balanced face is not only perceived as beautiful, but it is also free of health problems such as: dental malocclusions and tooth wear; facial underdevelopment (including facial asymmetry and craniofacial obesity); temporo-mandibular joint dysfunction (TMD), and upper airway difficulties, such as snoring, sleep disordered breathing, and obstructive sleep apnea (OSA). These conditions, whether diagnosed or covert, represent major issues in this field of work.

For example, traditional devices and treatments do not adequately address the underlying causes of poor tooth alignment. Poor tooth alignment is commonly accompanied by several other clinically-observable signs and symptoms, such as facial asymmetry, according to the patient's genome. One major issue not adequately addressed in the prior art teachings and traditional methods and devices is the irregular alignment of teeth as a result of development compensation. For example, malocclusion, an obvious sign of which is irregular teeth, belies a more serious issue, and may require correction and/or development of the bone constituting the jaws during comprehensive orthodontic care.

The current art does not fully treat the underlying cause by adequately interacting with or naturally-manipulating the genome because the traditional methods and devices do not recognize the importance of the gene-environmental interactions and, therefore, lack the structural elements necessary to properly signal the genes, which results in less than optimal corrections despite the temporo-spatial pattern or genetic template of facial development. Examples of common but detrimental environmental stimuli include myofunctional influences, such as bottle-feeding, a lack of breast-feeding, pacifier use, thumb-sucking, and other childhood habits including a soft diet of refined foods. Thus, dysfunctional features—such as adverse tongue posture, abnormal swallowing patterns, and lip activity—lead to further craniofacial consequences as the child matures (such as malocclusion). Yet, some of these consequences (such as obstructive sleep apnea) may not manifest until adulthood.

These consequences are the outcomes of gene-environmental factors that are thought to perturb the genetic craniofacial foundation encoded by genes, and include features such as a high-vaulted palate with maloccluded teeth, and functional features, such as a submandibular pannus (double chin). However, the complexity of these gene-environmental interactions leads to heterogeneity in terms of patient presentation. Thus, patients may present with a single feature, such as a malocclusion, TMD, snoring, wear facets on teeth, aged facial appearance, or any combination of the above, even though the underlying etiology is similar. For any foundational correction to remain stable, it must be co-provided with a functional correction.

More recently, biomechanical loading is thought to be an important regulator of osteogenesis, as bone formation occurs in response to its functional environment. Based on this information, biophysical techniques of osteo-stimulation have been successfully introduced into clinical practice.

These biophysical techniques include craniofacial distraction osteogenesis, and the application of ultrasound etc. to promote bone formation. As well, titanium implants are commonly used in orthopedics and dentistry. These implants integrate into the host's bone by a complex process known as osseo-integration. Data suggest that micromechanical forces may have anabolic effects on bone in-growth surrounding intra-osseous titanium implants.

For example, in one study micromechanical forces of 200 mN at 1 Hz were delivered axially to implants for 10 minutes per day for 12 consecutive days. The average bone volume near the mechanically loaded implants was significantly greater than the unloaded control side, and the average number of bone-producing osteoblast-like cells was significantly greater on the loaded side compared to the controls. There was also a significant increase in mineral apposition and bone-formation rate for the mechanically stressed implants compared to the controls. Therefore, modulation of bone in-growth can occur by in vivo micromechanical loading.

A considerable part of oral and maxillofacial surgery deals with bone healing. Recently, low-intensity ultrasound treatment has been shown to reduce the healing time of bone fractures. To observe the clinical effects of low intensity ultrasound after tooth extraction in patients, the sockets on one side were treated with low intensity ultrasound while the other side underwent no treatment. It was found that clinical use of low intensity ultrasound reduced post-operative pain and the incidence dry socket, and it also stimulated bone healing after extraction of mandibular third molar teeth. Therefore, the potential of ultrasound to stimulate maxillofacial bone healing may be of value in other orthopedic applications.

One study applied ultrasound to human gingival fibroblasts, mandibular osteoblasts, and monocytes. Ultrasound was found to induce cell proliferation in fibroblasts and osteoblasts by 35-50%. Collagen synthesis was also significantly enhanced (up to 110%) using a 45 kHz ultrasound device with intensities of 15 and 30 mW/cm2 (SA). In addition, angiogenesis-related cytokine production, such as IL-8, bFGF and VEGF were also significantly stimulated in osteoblasts. Therefore, therapeutic ultrasound induces in vitro cell proliferation, collagen production, bone formation, and angiogenesis.

Another known structure known in the prior art is sutures, which are fibrous connective tissue joints found between intramembranous craniofacial bones. They consist of multiple connective tissue cell lines, such as mesenchymal cells, fibroblasts, osteogenic cells, and osteoclasts. Sutures are organized with osteogenic cells at the periphery, producing a matrix that is mineralized during bone growth and development; with fibroblastic cells with their matrices in the center. Cyclic loading of these sutures may have clinical implications including acting as mechanical stimuli for modulating craniofacial growth and development in patients. One study demonstrated that in vivo mechanical forces regulate sutural growth responses in rats. In that study, cyclic compressive forces of 300 mN at 4 Hz were applied to the maxilla for 20 minutes per day over 5 consecutive days. Computerized analysis revealed that cyclic loading significantly increased the average widths of the sutures studied in comparison with matched controls, and the amount of osteoblast-occupied sutural bone surface was significantly greater in cyclically loaded sutures. These data demonstrate that cyclic forces are potent stimuli for modulating postnatal sutural development, potentially by stimulating both bone formation (osteogenesis) and remodeling (osteoclastogenesis).

In a similar study, static and cyclic forces with the same magnitude of 5N were applied to the maxilla in growing rabbits in vivo. Bone strain recordings showed that the waveforms of static force and 1 Hz cyclic force were expressed as corresponding static and cyclic sutural strain patterns. However, on application of repetitive 5N cyclic and static forces in vivo for 10 minutes per day over 12 days, cyclic loading induced significantly greater sutural widths than controls and static loading. Cell counting also revealed significantly more sutural cells on repetitive cyclic loading than sham control and static loading.

Fluorescent labeling of newly formed sutural bone demonstrated more osteogenesis on cyclic loading in comparison with sham control and static loading. Thus, the oscillatory component of cyclic force, or more precisely the resulting cyclic strain experienced in sutures, is a potent stimulus for sutural growth. The increased sutural growth by cyclic mechanical strain suggests that both microscale tension and compression induce anabolic sutural growth response. Therefore, mechanical forces readily modulate bone growth, and cyclic forces evoke greater anabolic responses of craniofacial sutures and cartilage.

In another study, the premaxillo-maxillary sutures of growing rabbits received in vivo exogenous static forces with peak magnitudes of 2N, or cyclic forces of 2N with frequencies of 0.2 Hz and 1 Hz. The static force and two cyclic forces did not evoke significant differences in the peak magnitude of static bone strain. However, cyclic forces at 0.2 Hz delivered to the premaxillo-maxillary suture for 10 minutes per day over 12 days (120 cycles per day) induced significantly more craniofacial growth, marked sutural separation, and islands of newly formed bone, in comparison with both sham controls and static force of matching peak magnitude.

This data demonstrates that application of brief doses of cyclic forces induces sutural osteogenesis more effectively than static forces with matching peak magnitude. Sutural growth is accelerated upon small doses of oscillatory strain (600 cycles delivered 10 minutes per day over 12 days), and both oscillatory tensile and compressive strains induce anabolic sutural responses beyond natural growth. Oscillatory strain likely modulates genes and transcription factors that activate cellular developmental pathways via mechanotransduction pathways. And, sutural growth is determined by hereditary and mechanical signals via gene-environmental interactions or epigenetics. Therefore, small doses of oscillatory mechanical stimuli have the potential to modulate sutural growth for therapeutic objectives.

The above data suggest that oro-facial sutures have capacities for mechanical deformation. The elastic properties of sutures are potentially useful for improving our understanding of their roles in facial development. Current data on suture mechanics suggest that mechanical forces regulate sutural growth by inducing sutural mechanical strain. Therefore, various orthopedic therapies, including orthodontic functional appliances, may induce sutural strain, leading to modification of natural sutural growth.

Additionally, for example, Singh G. D., Diaz, J., Busquets-Vaello, C., and Belfor, T. R. in "Soft tissue facial changes following treatment with a removable orthodontic appliance in adults," *Funct. Orthod.*, (2004) vol. 21 no. 3 at pp. 18-23 reported dental and facial changes in adults treated with a static removable orthodontic appliance (and as disclosed in United States Patent Application No. 2007/0264605 published on 15 Nov. 2007 and as disclosed in U.S. Pat. Nos. 7,314,372 issued on 1 Jan. 2008 and 7,357,635 issued on 15 Apr. 2008, the full disclosures of which are hereby incorporated by reference as if set out fully herein). The maxillary arch showed a 30-percent relative size increase in the mid-palatal region (corresponding to the mid-palatal suture) with shape changes consistent with improved dental alignment and maxillary expansion in the transverse direction. However, the treatment time was excessively long (up to 30 months in one case). Nevertheless, current orthodontic and dentofacial orthopedic therapies exclusively utilize static forces to change the shape of craniofacial bones via mechanically induced bone apposition and resorption, but cyclic forces capable of inducing different sutural strain wave forms may accelerate sutural anabolic or catabolic responses.

Recently, it was shown that low intensity pulsed ultrasound enhances jaw growth in primates when combined with a mandibular appliance, and that orthodontically induced root resorption can be repaired using ultrasound in humans.

Thus, there remains a need for improved treatment methods, systems, and devices that utilize therapy that harness the underlying developmental mechanisms—encoded at the level of the gene. Further, such improved treatment methods, devices, and systems should utilize the application of brief doses of cyclic forces to induce sutural osteogenesis. Additionally, there remains a need for a removable orthopedic-orthodontic appliance with cyclic functionality and a system and method to bioengineer vibrational orthopedic-orthodontic devices.

Further, teeth are adept at adapting to axial stimuli preferentially through physiologic mechanisms. These developmental mechanisms include active tooth eruption, passive tooth eruption; and the tooth support phenomenon. For example, when a deciduous tooth is lost, the permanent successor will typically actively erupt in an axial direction until it makes contact with an opposing tooth or teeth. Similarly, when a tooth is extracted, the opposing tooth can passively erupt until it meets some hindrance.

In the tooth support phenomenon, teeth undergo an initial elastic intrusion when an axial force is applied; and a further visco-elastic intrusion if the force is maintained, for example during mastication. When the axial force is removed, the tooth undergoes initial elastic extrusion and further visco-elastic extrusion (recovery) so that the tooth returns to its original position, in balance or in equilibrium with the opposing tooth/teeth. However, when an orthodontic device is applied to a tooth these natural mechanisms of homeostasis can be overpowered.

In contrast, during the development of the dentition, commonly referred to as tooth eruption, it is now thought that inherited genes are transcribed and expressed. The timing and orderly eruption of teeth is genetically-encoded in a developmental mechanism that is part of a systemic phenomenon called temporo-spatial patterning. In other words, specific teeth develop at specific sites at specific times. Thus, there is an innate, physiologic mechanism of tooth alignment that can be overpowered by biomechanical orthodontic therapy.

Moreover, current research in molecular genetics suggests that external stimuli can cause the expression of genes that are not normally expressed. Therefore, the application of appropriate external stimuli to teeth that have already completed their eruptive phase can cause these teeth to take up new positions in accord with the patient's genome as determined by temporo-spatial patterning, using the patient's own natural genome. Bearing in mind that teeth are adept at adapting to stimuli in the axial direction, the spring design described herein is orientated at an angle approximately parallel to the long axis of the palatal/lingual surface of the tooth, unlike all previous designs that contact the palatal/lingual surface of the tooth in the transverse plane.

Conventional orthodontic therapy is based on the premise that when a force is applied to a tooth, the tooth will move in response to the force. Thus, conventional fixed orthodontic approaches are primarily based upon the manipulation of teeth by exerting, controlling and maintaining forces, vectors and moments on teeth and/or roots. This torque control can be exerted on teeth either individually, segmentally or by the use of wires that engage the entire dental arch through the use of brackets.

In order to apply corrective forces, sophisticated systems of brackets and wires are commonly deployed. Brackets and/or bands of various designs are directly bonded to the surfaces of the teeth. The brackets have slots at various orientations that can engage wires. The wires are also of different materials, such as stainless steel and/or other alloys such as Nickel-Titanium; and of different cross-sectional shapes, such as round, square or rectangular; and of different sizes e.g. 0.016 inch round and 0.018 by 0.022 inch rectangular etc.

The wires are ligated to the brackets in various ways to permit low-friction, sliding mechanics, for example. Typically, the first phase of this biomechanical orthodontic correction is leveling using round wires, followed by more detailed tooth re-orientation using rectangular or square wires. Other corrections, such as space closure, are often accomplished by using elastics attached to the brackets or coil springs along the arch-wire to pull or push teeth into positions as determined by the orthodontic clinician.

From the patients' viewpoint, apart from esthetic considerations, one of the drawbacks of conventional fixed appliances is the trauma that the metallic orthodontic components and/or elastics may cause. The inside surface mucosa of the cheeks and lips, as well as the tongue, routinely contacts the metallic orthodontic components and/or elastics during swallowing, speech and mastication, which can cause cheek-biting, painful mouth ulcers, etc. In addition, inappropriate forces and moments that reach or exceed physiologic blood pressure during fixed orthodontic treatment can cause root resorption, by producing stresses in the periodontium. To avoid high pressures, the acting forces need to remain below about 0.5N. These levels of forces can be achieved by using Nickel-Titanium (NiTi) wires with a diameter of 0.012-inches, for example. The use of NiTi wires ensures an almost constant moment (torque) based on its stiffness, spring-back, shape memory, and elasticity. A superior NiTi alloy wire was developed by the Furukawa Electric Co., Ltd., Japan. This Japanese NiTi wire exhibits "super-elasticity" in that this particular wire delivers a constant force over an extended portion of its deactivation range. This Japanese NiTi alloy wire undergoes minimal permanent deformation during activation, and its stress remains nearly constant despite the change in strain within a specific range. This unique feature is called 'super-elasticity'. Moreover, Titanium-Niobium-Aluminum (Ti—Nb—Al) springs generate lighter and more continuous forces. Thus, Ti—Nb—Al wire has superior mechanical properties for smooth, continuous tooth movement, and Ti—Nb—Al wire may be used as a nickel-free, shape-memory and super-elastic alloy wire for orthodontic tooth movement instead of Ni—Ti wire.

Similarly, NiTi coil springs, used with elastic chains, can generate nearly constant forces over a wide range of activation due to low load deflection. Reducing the load deflection rates of orthodontic springs is important, as it provides relative constancy of the moment-to-force ratio applied to the teeth with concomitant, predictable tooth movements. Lower load deflection rate springs increase patient comfort and reduce the number of office visits, while lowering potential tissue damage.

Using 0.016"×0.022" NiTi and multi-stranded arch wires employed in a 0.018" slot system, with power-hooks or up-righting springs, bodily tooth movements can be achieved. But, friction may increase if the up-righting torque is too strong and other unwanted side effects such as tooth extrusion, rotation and tipping can also occur. Therefore, the load-deflection rate of an orthodontic spring depends on the modulus of elasticity of the utilized alloy and the geometric configuration of the spring. Thus, it is usually preferable to choose springs with a low load-deflection rate of about 50 p/mm (50 kN/mm$^2$). Nevertheless, it has been found that the force systems produced by straight wire and conventional up-righting springs can show severe extrusive force components, which may lead to occlusal trauma. Furthermore, intra-oral adjustment of up-righting springs is difficult because of high susceptibility to minor modifications of geometry.

Prior art had described the design and construction of the stainless steel flap springs utilized, including springs constructed of heat-treated alloy wire transversely orientated against the palatal/lingual surfaces of the pertinent teeth. Nevertheless, palatal finger springs; open springs; boxed springs; cranked palatal springs; re-curved springs, double cantilever or Z-springs, and T-springs etc. that are transversely orientated against the palatal/lingual or mesial/distal surfaces of the pertinent teeth are commonly found in the orthodontic literature as known by those skilled in the art. Indeed, the use of acrylic buttons attached to the palatal/lingual surfaces of pertinent teeth has been commonly deployed to prevent the transversely orientated spring from riding up the palatal/lingual tooth surface.

Thus, there remains a need for improved treatment methods, systems, and devices that utilize springs that harness the underlying developmental mechanisms—encoded at the level of the gene. Further, such improved treatment methods, devices, and systems should utilize cyclic intermittent forces to induce sutural osteogenesis. Additionally, there remains a need for a spring with cyclic functionality as a key component of a system and method to bioengineer vibrational orthopedic-orthodontic devices.

SUMMARY OF THE INVENTION

The present invention provides a device, system, and treatment method for correcting common orthodontic and craniofacial abnormalities. In one preferred embodiment, the present invention includes a vibrational orthopedic-orthodontic appliance adapted to induce craniofacial homeostasis by triggering the patient's genome. One objective of the invention is to increase, enhance, optimize and augment craniofacial homeostasis, equilibrium and balance.

The present invention further contemplates a system comprising a device including a removable orthodontic appliance with active plates. Its framework is a base plate made from acrylic or a similar (thermoplastic) material. The appliance or device comprises an acrylic body that incorporates various components within its two halves as shown in FIG. 1.

This component serves as a base in which the various components are embedded and onto which clasps, bands or bonded brackets are attached directly or indirectly (FIG. 2).

The active elements of the device can be vibrational, ultrasonic or oscillatory components with an actuator or other expansion mechanism that straddles the two parts of the body plate (FIG. 3).

The tooth-contacting material can be high-elasticity, preformed alloys that are custom-formed to adapt to the long axis of the palatal/lingual surfaces of the teeth. These materials can be adjusted as required by the clinician.

Alternatively, electrical ultrasonic/vibrational, meso-motors or micro-motors can be located between the two halves of the body plate. These ultrasonic/vibrational motors can have their characteristics varied manually or through the use of a microprocessor, chip or programmable integrated circuit.

In addition, these small electrical motors adjust the separation of the two plate halves automatically through the use of pressure sensors in contact with several tooth surfaces to ensure the device remains in contact with the tissues without having to manually adjust the appliance. These sensors can be used to monitor, download and measure the pressure applied to each tooth or groups of teeth. The sensors can be located in other positions, such as the body plate to record readings in the roof of the mouth or floor of the mouth, and to provide soft tissue pressure measurements. In addition, by using a global positioning system changes in tooth position could be monitored, downloaded and measured for calculations and predictive modeling of changes using appropriate computer software.

Further adjustments can then be made by applying an electric current to the micro- or meso-motors, assisted by the readings of the output of the sensors and/or the global positioning system. For these reasons, a microprocessor will be provided embedded within the body plate.

To power the microprocessor, a battery or cell is also provided, similar to those used for hearing aids or bone conductors. The microprocessor is supplied via conducting wires with information from the pressure sensors, and its output can drive the ultrasonic/vibrational, micro-motors or meso-motors, via other conducting wires at least partially embedded in the plastic body, in order to automatically keep the vibrational pressure on the teeth and tissues at a pre-set level. Furthermore, the dental healthcare provider can create a therapy profile that will lead to a good outcome for each patient. For example, the force vectors need to be cyclic, intermittent, long-acting, low-level and consistent so as not to over do the application of force and produce an inferior result. This profile may be in the form of data or digital codes stored in a memory that is part of the microprocessor. Thus the microprocessor would control the motors based on the profile data and the readings from the sensors.

The intra-oral device is attached to at least two permanent or deciduous teeth using clasps, bands or direct bonding to the surfaces of the teeth with orthodontic brackets. A labial bow and other wires in the form of springs can also be provided as required. The body of the device lies in close approximation to the patient's tissues, especially in the palate in the maxillary version of the appliance; and on the lingual areas in the mandibular version of the appliance. In addition, extensions of the plate body symmetrically overlay the biting (occlusal) surfaces of at least two of the patient's teeth in the space where those teeth would normally contact the opposing teeth from the upper or lower jaw. The thickness of the occlusal coverage ranges from approximately 0.5 mm to approximately 5.0 mm, as determined by orthodontic equilibration, and may be absent in certain locations or spots, if required. The plate body itself has a thickness that varies, and ranges from about 1.0 mm to about 5.0 mm, depending upon the components embedded within it.

Micromechanical, cyclic, tensile and/or compressive forces and/or doses of oscillatory strain will be applied using an ultrasonic/vibrational component similar to that found in ultrasonic dental scalers, electric toothbrushes, ultrasonic dental cleaning appliances and cellular telephones. The range of force applied will be very low and vary between 0.1-10N although forces of other magnitudes may be applied as required. The frequency applied will vary between 1-600 Hz although other ranges of cycles may be applied as required.

The device will be activated for 10-60 minutes per day although other durations of application may be used as required. The overall duration of the ultrasonic/vibrational therapy will last between 5-14 consecutive days or non-consecutive days e.g. alternate days, although other durations of therapy will be used as required, depending on the patient's response, as it is thought that frequent small activations of a midline screw-mechanism or actuator are more effective than a few large ones.

The device may be used in conjunction with conventional fixed orthodontic appliances (braces), if required. It may also be used as a component in a two-phase orthopedic-orthodontic treatment. The device should be equally applicable to child, teenage and adult dental patients.

One preferred embodiment includes two or more retentive (Adams or Delta or Crozat) clasps to hold the appliance in place while it is being worn. These Adams or Delta or Crozat clasps are attached to the molar teeth and provide good retention.

In one preferred embodiment the appliance includes a passive acrylic baseplate connecting the two halves with an intervening midline jack-screw. In an alternate preferred embodiment the appliance includes a memory- or posture-pedic smart material for the baseplate. This active baseplate will help remodel the underlying bone as tooth movement proceeds.

Another preferred embodiment of the present invention includes a method for achieving concurrent craniofacial correction, combining simultaneous orthopedic and orthodontic therapies without the use of typical biomechanical forces. The method comprises:

(a) introducing appliances into the oral cavity that alter the spatial relations or the bite of the jaws and teeth;

(b) adjusting the appliances to achieve intimate contact with oral structures, including the teeth, but without the use of force that push or pull on the teeth;

(c) inducing an intermittent, non-continuous, cyclic stimulus or stimuli that reach a physiologic threshold to evoke mechanoreceptors present within craniofacial sutures, including the periodontium;

(d) permitting tissue remodeling to occur such that the appliances lose intimate contact with oral structures, including the teeth; and (e) re-adjusting the appliance or appliances to re-establish intimate contact.

This method is further adopted to include adjusting the amount of correction relative to an individual patient's genome. Additionally, the time of correction depends on the individual's genome. Notably, this method does not require the application of orthodontic brackets to the teeth. However, in an alternative embodiment, the present method adapts to cooperate with orthodontic brackets applied to the teeth. In yet another alternative preferred embodiment, the method adapts to cooperate with orthodontic wires applied to orthodontic brackets applied to the teeth.

One possible device or appliance according to another preferred embodiment of the present invention includes an orthopedic-orthodontic appliance for inducing remodeling of craniofacial hard and soft tissues comprising:

(a) a removable oral appliance composed of a discontinuous hard acrylic base plate wherein the discontinuous hard acrylic includes extensions overlaying an occlusal surface of posterior teeth bilaterally;

(b) a tooth contacting material, which is anchored to the hard acrylic and contacts the palatal/lingual surface of at least one tooth; wherein the contacting material has the ability to produce and transmit intermittent, cyclic signals to said palatal/lingual surface of said tooth; and (c) a midline medio-lateral actuator, which permits separation of said two halves of hard acrylic, wherein the hard acrylic includes clasps, which are anchored to said hard acrylic and attach to said posterior teeth bilaterally.

Further, this contacting material is a wire composed of a single strand of alloy. Alternatively, the contacting material is a braided wire composed of a plurality of strands of alloy. In yet another preferred embodiment, the contacting material is orientated at an angle approximately parallel to the long axis of said tooth.

In yet another preferred embodiment, the oral appliance includes a contacting material comprising a lever arm of a vibrational meso-motor capable of producing intermittent, cyclic signaling.

In yet another preferred embodiment, the oral appliance further includes a vibratory signal contacting the palatal lingual surface of one tooth is produced by ultrasonic technology.

Additionally, the acrylic overlay of posterior teeth bilaterally is about 5 mm in thickness or less. And, the vibratory signal is produced by intermittent contact of opposing teeth in the maxillary and mandibular dental arches, during sleep, swallowing, speech and mastication, for example.

In yet another preferred embodiment, a three-dimensional (3-D) axial spring design is described wherein said spring is orientated at an angle approximately parallel to the long axis of the palatal/lingual surface of the tooth and/or root (see FIG. 4). Said 3-D axial spring lies on palatal/lingual surface of the contiguous oral structures (mucosa) orientated at an angle approximately parallel to the long axis of the palatal/lingual surface of the tooth and/or root (see FIG. 4). FIG. 5 illustrates the three axes, including transverse (from side to side across the tooth), antero-posterior (from the front biting edge of the tooth back towards the gum), and vertical (spring loops extending up away from the tooth, and down towards the tongue).

The 3-D axial spring design wherein the active (compression-extension) axis of the spring is orientated at an angle approximately parallel to the long axis of the palatal/lingual surface of the tooth and/or root, instead of it lying approximately parallel to the transverse axis of the palatal/lingual surface of the crown of said tooth is described. The initial arm 30 of said 3-D axial spring is embedded in a discontinuous acrylic base-plate, and the terminal arm 30 of said 3-D axial spring is embedded in said acrylic base-plate, both arms 30 lying in approximately the same vertical axis. Said initial arm 30 and said terminal arm 30 are connected by a plurality of undulating U-bends that comprise the body of said 3-D axial spring. Said plurality of U-bends may vary in amplitude, being bigger or smaller in size. Said plurality of U-bends may vary in frequency, being many or few in number. Said plurality of U-bends may vary in characteristic, being differently shaped, such as a 'Z' formation or a square waveform etc. Said plurality of U-bends in said initial and said terminal arms 30 of said body of said 3-D axial spring lie in close approximation with respect to each other for the entire length of said active (compression-extension) axis of said 3-D axial spring. Said 3-D axial spring lies on palatal/lingual surface of the contiguous oral structures (mucosa) orientated at an angle approximately parallel to the long axis of the palatal/lingual surface of the tooth and/or root (see FIG. 4). The head of said 3-D axial spring intimately contacts the long axis of said palatal/lingual surface of said tooth (see FIG. 4).

The three-dimensional (3-D) axial spring design as in FIGS. 5A, 5B, and 5C whereby a plurality of said 3-D axial springs are orientated approximately parallel to the long axis of said palatal/lingual surface of said tooth/root or a plurality of said teeth/roots (see FIG. 3).

The 3-D axial spring design wherein one active (compression-extension) arm 30 of said 3-D axial spring is orientated at an angle approximately parallel to the long axis of the palatal/lingual surface of the tooth and/or root, and the other active (compression-extension) arm 30 of said 3-D axial spring is lying approximately parallel to the transverse axis of said palatal/lingual surface of the crown of said tooth. The initial arm 30 of said 3-D axial spring is partially or fully embedded in a discontinuous acrylic base-plate, and the terminal arm 30 of said 3-D axial spring is embedded in said acrylic base-plate, both arms 30 lying at approximately 90-degrees or less with respect to each other (see FIG. 3). Said initial arm 30 and said terminal arm 30 consist of and are connected by a plurality of undulating U-bends that comprise the body of said 3-D axial spring. Said plurality of U-bends may vary in amplitude, being bigger or smaller. Said plurality of U-bends may vary in frequency, being many or few. Said plurality of U-bends may vary in characteristic, being differently shaped. The arrangement of said plurality of U-bends is in an open configuration for the entire length of said active (compression-extension) arms 30 of said 3-D axial spring. Said initial arm 30 of said 3-D axial spring lies on palatal/lingual surface of the contiguous oral structures (mucosa) orientated at an angle approximately parallel to the long axis of the palatal/lingual surface of the tooth and/or root (see FIG. 4). Said terminal arm 30 of said 3-D axial spring is orientated at an angle approximately parallel to said transverse axis of said palatal/lingual surface of said tooth, not contacting any hard or soft tissues; however, head of said active (compression-extension) arm 30 of said 3-D axial spring orientated at an angle approximately parallel to said transverse axis of said palatal/lingual surface of crown of said tooth, lies in intimate contact with said palatal/lingual surface of crown of said tooth.

The 3-D axial spring design as in FIGS. 5A-5C whereby a plurality of said 3-D axial springs are interconnected by a plurality of U-bends approximately parallel to the long axis of said palatal/lingual surface of said tooth/root or a plurality of said teeth/roots, said plurality of U-bends lying on palatal/lingual mucosa of said teeth and/or roots (see FIGS. 3 and 4).

DRAWING

FIG. 12 illustrates a patient's teeth before the device and method of the current invention was applied.

FIG. 13 illustrates a patient's corrected teeth after the device and method of the present invention was applied.

DESCRIPTION OF THE INVENTION

Figure 1:
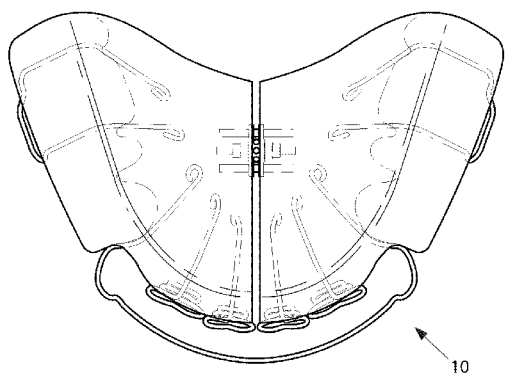
FIG. 1 is a bottom view of a device according to a preferred embodiment of the present invention.

Possible preferred embodiments will now be described with reference to the drawings and those skilled in the art will understand that alternative configurations and combinations of components may be substituted without subtracting from the invention. Also, in some figures certain components are omitted to more clearly illustrate the invention.

The present invention, in a first preferred embodiment, includes a treatment method including the following procedures:

The clinician should first be able to visualize the effects of ideal facial development for a given patient. Next, a clinical examination of the head, neck and facial area is performed followed by a postural evaluation. Diagnostic imaging is then performed using lateral cephalographs, panoral radiography, computerized tomography, Cone-beam CT scan, and/or MRI. Photographic images are also taken intra-orally, extra-orally, and posturally. Three-dimensional techniques such as stereophotogrammetry or laser scan should also be performed.

Subsequent to medical imaging, an electro-diagnostic analysis is performed using Joint Vibrational Analysis (JVA), Electromyography (EMG), and Electrognathology (EGN).

Impressions of the maxillary and mandibular arches should be taken to produce study models, which can be laser scanned to create digital study models.

Prior to the induction of craniofacial homeostasis, a treatment protocol is developed with the goal of visualizing the treatment objective.

The foregoing treatment plans need to be based on what is termed the osteogenetic-orthodontic concept, i.e., the growth and development of the craniofacial region can be influenced by signaling using an osteogenetic-orthodontic appliance. Data-driven predictive modeling with computer analyses may be utilized where available.

The following steps must be followed prior to the induction of craniofacial homeostasis: Evaluation of facial features should include assessments of: facial asymmetry, intercanthal angle, sclera, venous pooling, and lower eyelid of the patient. The vertical and antero-posterior axes of the ears should be noted. Asymmetry of the nares, morphology of the dorsum, and relative size of the nose should be noted, including the depth of the nasolabial grooves. The form of the lips should be examined for: asymmetry, thin upper lip, dry and/or everted lower lip, and the depth of the labiomental groove.

Facial profile analysis should include: frontonasal angle, cranial base length, facial proportions, under-developed midface/maxilla with or without midfacial retrognathia, under-developed mandible with or without retrognathia (retruded position).

Esthetic Line of the face is assessed. This is the measurement of the midface in relation to the cranial base, and represents the fullness of the facial profile. It is the distance from the tip of the nose to the incisal edge of the upper incisor in the midline. This measurement should be approximately 38 mm in adults.

Protocol for the Induction of Craniofacial Homeostasis:

With the foregoing steps accomplished, the next step is the foundational correction treatment protocol by which facial development for maximum medical improvement is enhanced by achieving skeletal and dental balance, equilibrium and homeostasis.

The desired results from a successful protocol are: 1) Correcting the size and shape of the maxilla; 2) Correcting the size, shape and position of the mandible; and, 3) Bringing the mandible into occlusion with the maxilla, and maintaining the corrected spatial relations (including the posture of the tongue, lips etc.).

Treatment Planning:

Proper treatment planning will take into account the following: 1) Correcting skeletal midline to soft tissue midline; 2) Correcting occlusion to Class I molar/cuspid relationship; and, 3) Correcting condyles to symmetrical positions.

For patients having space less than 2 mm (Class I Christiansen effect):

Step 1. Development of Maxilla

Insert upper osteogenetic-orthodontic appliance with snug or intimate fit;

Occlusal coverage should be adjusted to avoid open-bite; anterior teeth should be edge to edge;

Wear osteogenetic-orthodontic appliance at night-time, or additionally as indicated;

Turn screw approximately once per week (abut 0.25 mm), or more or less as required. If maxilla is not ready for the turn, the patient should wait until it is ready (i.e. when the appliance feels loose).

Step 2. Development of Mandible

Upper appliance should be used for about 3 to about 6 months (or as required) before insertion of lower appliance.

Insert lower osteogenetic-orthodontic appliance with snug or intimate fit.

Stop developing the maxilla but have patient continue to wear the upper appliance.

Mandible should be developed until it occludes with the maxillary arch.

Turn screw approximately once per week (about 0.25 mm, or more or less as required in a particular patient's case). If mandible is not ready for the turn, the patient should wait until it is ready (i.e. when the appliance feels loose).

For Steps 1 and 2:

Try to avoid complete buccal crossbite during development.

Anterior 3-D axial springs are activated to re-position teeth to ideal esthetic line measurement, approximately.

3-D axial springs are activated for tooth alignment, if needed.

Step 3. Finish Treatment

Adjust upper and lower appliances simultaneously until optimally-desired results are reached.

Balance any facial asymmetries as far as possible

Step 4. Retention

Maintain balance;

Continue using osteogenetic-orthodontic appliance(s) at night only.

For Steps 1-4:

Rate of development depends on individual; and

Time of treatment depends on rate of development.

For patients having space more than 2 mm (Class II Christiansen effect):

Step 1. Development of Maxilla

Insert upper osteogenetic-orthodontic appliance with snug fit.

Patient continues using day-time orthotic repositioning appliance for day wear, including eating.

As maxilla develops, adjust day-time re-positioner appliance as required.

If patient wakes up with pain, construct an NTI appliance (night orthotic) for use during sleep.

Turn screw approximately about once per week (about 0.25 mm), or as required (more or less frequently). If maxilla is not ready for the turn, the patient should wait until it is ready (i.e. when the appliance feels loose).

When Christiansen effect is 2 mm or less, construct lower osteogenetic-orthodontic appliance Step 2. Development of Mandible Insert lower osteogenetic-orthodontic appliance with snug fit.

Remove day-time re-positioner appliance.

Stop developing the maxilla.

Turn screw approx. once per week (0.25 mm). If mandible is not ready for the turn, the patient should wait until it is ready (i.e. when the appliance feels loose).

Mandible should be developed until it occludes with the maxillary arch.

For steps 1-2.

Rate of development depends on individual.

Time of treatment depends on rate of development.

Avoid complete buccal crossbite.

Activate anterior 3-D axial springs for tooth alignment as needed.

Step 3. Finish Treatment

Adjust upper and lower appliances simultaneously until optimally-desired results are reached.

Balance any facial asymmetries as far as possible.

Step 4. Retention

Maintain balance.

Continue using osteogenetic-orthodontic appliance(s) at night only.

The Functional Correction treatment protocol is directed toward enhancing facial development by achieving extra-oral (facial) and intra-oral soft tissue balance, equilibrium and homeostasis for maximum medical improvement. This is achieved through: 1) Developing the muscles of the face (muscles of facial expression); 2) Developing the muscles of the jaws (muscles of mastication); 3) Maintaining corrected spatial relations (posture of tongue, lips etc.); and, 4) Losing features of craniofacial obesity where indicated.

A treatment plan is developed which takes into account: 1) Correcting extra-oral soft tissues; 2) Correcting intra-oral soft tissues; and, 3) Correcting tongue posture to enhance functional airway space.

Figure 10:
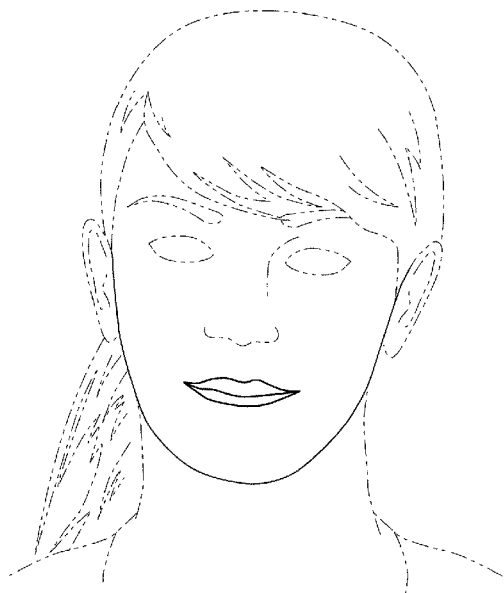
FIG. 10 is a "before" drawing of a patient.
Figure 11:
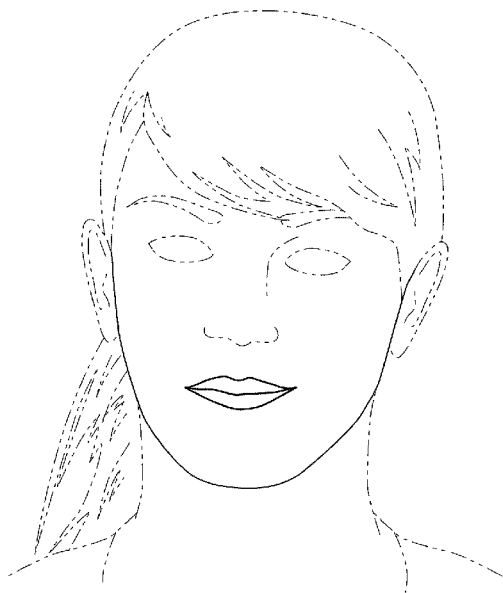
FIG. 11 is an "after" drawing representing the patient of FIG. 10 after a method according to the present invention was applied.
Figure 14:
FIG. 14 is a side view of a patient before the device and method of the current invention was applied.
Figure 15:
FIG. 15 is a side view of a patient after the device and method of the present invention was applied.

The method developed includes facial therapy to workout facial muscles approximately 10 mins. per day and oral myofunctional therapy to correct oral muscles, including the tongue. This treatment method just described results in before and after conditions of the patient as exemplified in FIGS. 10-11, for example.

In a second preferred embodiment, and well-suited for use with the treatment method previously described, the present invention includes an orthodontic device or appliance 10 of FIGS. 1-6.

Figure 2:
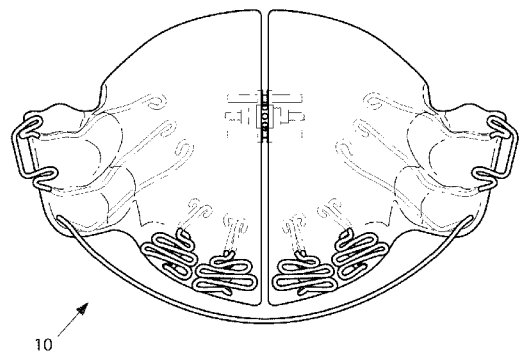
FIG. 2 is a top view of the device of FIG. 1.
Figure 3:
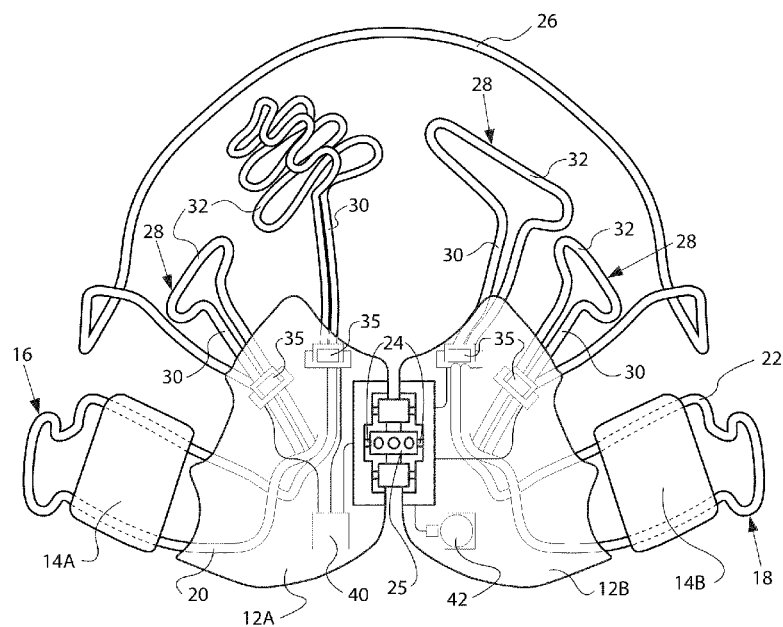
FIG. 3 is a bottom view of an alternative embodiment according to the present invention.
Figure 4:
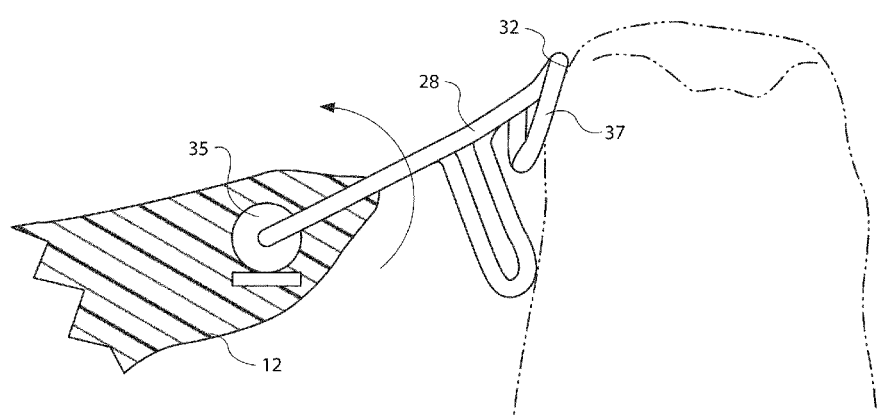
FIG. 4 is a partial side view showing the embodiment of FIG. 3 in relationship to a tooth of a patient.

FIGS. 1, 2 and 3 show an orthodontic device or appliance 10 of the split palate type in accordance with one preferred embodiment of the present invention. Device 10 includes a plate body 12, preferably of plastic material, such as acrylic. The plate body is preferably in two halves 12A, 12B, but it can be in one piece or in several pieces of unequal size. Plate body 12 has overlay 14 extending from it to a position that would cover the top of a tooth. While it is shown with one such overlay 14A on the left side in FIG. 3, it should be understood that the overlay 14B is on the right side. The location and extent of the overlay 14 is based on a clinical determination by the dental health care provider to achieve the desired equilibration in an optimal way.

A first clasp 16 and a second clasp 18 are connected to the plate; preferably by being embedded in the plastic material of plate body 12. Each clasp 16, 18 includes an archway 20, 22 for selectively permitting device 10 to be fitted about a tooth, preferably one of the posterior teeth, to hold the device or appliance in place. When fitted or connected, overlay 14A may be positioned to extend over one of the archways (archway 20 is shown in FIG. 3, with overlay 14B additionally extending over archway 22) so as to be in contact with the teeth. Overlay 14 is preferably placed on top of the teeth adjacent to archway 20 or 22 of the respective clasp 18, 20, thereby preventing the jaw from fully closing.

The halves 12A, 12B of plate body 12 may be connected by an expansion jack screw 24. While the screw 24 may be manually adjustable to control the separation of the plate halves, a small electrical micro-motor 25 may incorporate the screw 24 and be used to adjust the separation.

A labial bow 26, in the form of an arch wire, is also connected to the plate body 12, preferably by being embedded in the plastic material of the plate body 12. Labial bow 26 wraps around the front of the teeth and additionally acts to keep device 10 in place.

Figure 5A:
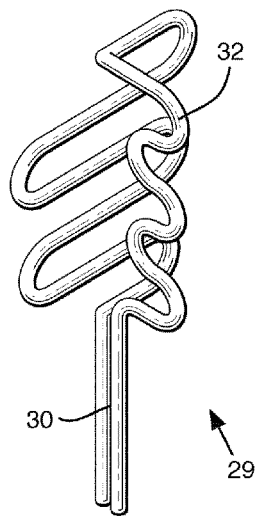
FIG. 5A is an offset frontal view of a three-dimensional axial spring device and method according a preferred embodiment of the present invention.
Figure 5B:
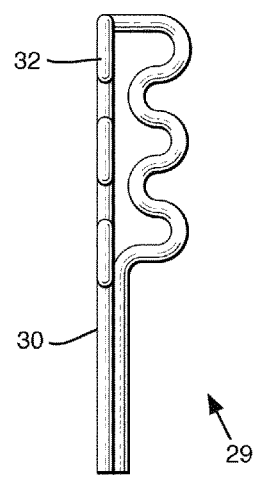
FIG. 5B is a side view of the 3-D axial spring of FIG. 5A.
Figure 5C:
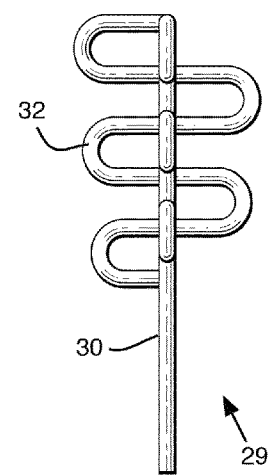
FIG. 5C is a top view of the 3-D axial spring of FIG. 5A.
Figure 6:
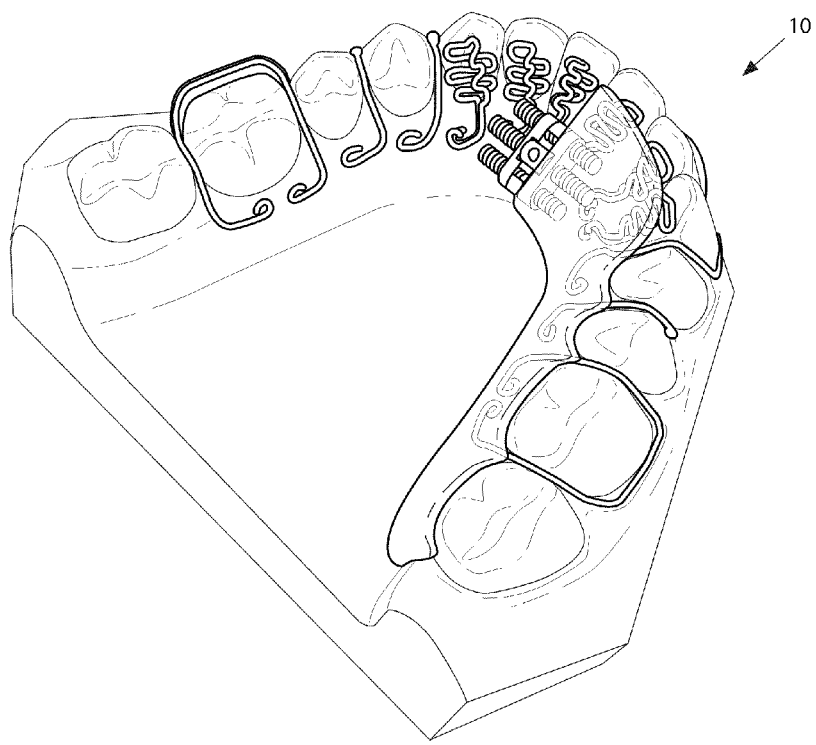
FIG. 6 shows a device according to a preferred embodiment of the present invention used to treat the lower jaw and teeth of a patient.
Figure 7:
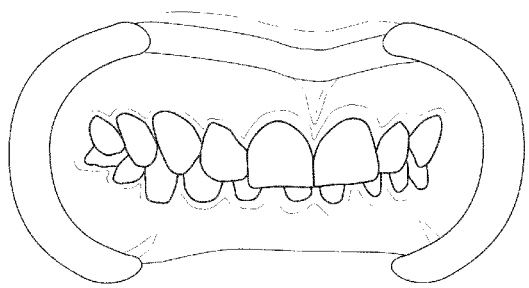
FIG. 7 illustrates a patient's teeth at the beginning of treatment according to a method of the present invention.
Figure 8:
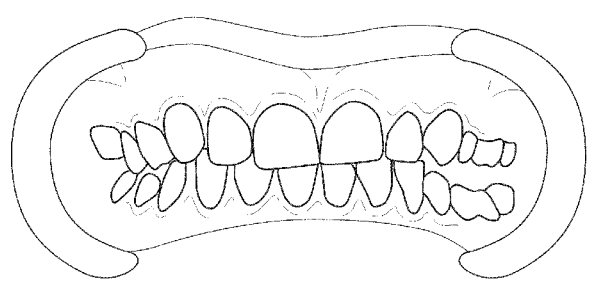
FIG. 8 illustrates the patient of FIG. 7 after one week of the treatment method.
Figure 9:
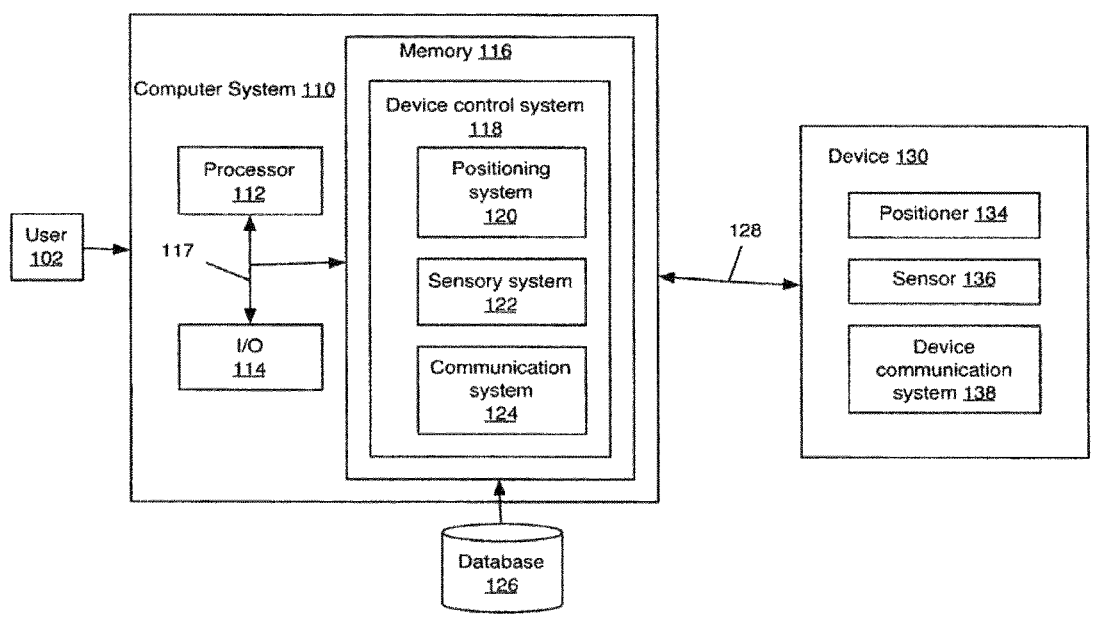
FIG. 9 is a representational diagram of a computer system according to one embodiment of the present invention.

A plurality of 3-D axial springs 28, which are also known in the art as Singh springs in FIG. 2, for example—or in an alternative preferred embodiment as the Singh spring 29 shown in FIGS. 5A, 5B, and 5C, for example—are coupled or otherwise connected to the plate body, preferably by being embedded in the plastic material of the plate body 12. Each 3-D axial spring 29 includes an arm portion 30 and a head portion 32. As is common, the head portion 32 rests against the inside of the teeth and contacts the patient's tissues at that location. Typically, the amount of contact can be adjusted by manual bending of the arm portions 30.

As an alternative, small electrical motors 35 can be located between the body plate 12 and one or more of the 3-D axial springs 28 to adjust the contact that the 3-D axial springs have to the patient's teeth and tissues without having to manually bend the springs. In addition, sensors can be located at the ends of the 3-D axial springs where they meet the teeth in order to measure the pressure applied to each tooth or group of teeth by the 3-D axial spring. The sensor can be located in other positions, but in such a case it would not provide a direct measurement of the pressure and some calculation would be necessary to arrive at the actual pressure.

During use of the device, as the jaw expands and other bones develop, it will be necessary to adjust the separation of the body plates 12A, 12B, as well as the contact of the 3-D axial springs, in order to continue the development of the bones. This can be accomplished during periodic visits, e.g., once a week, to the dental health care provider for adjustments. Such adjustments can be manual or, where the motors 25, 35 are present, they can be made by applying an electric current to the motors. In part, the output of sensors can be read by the dental health care provider to better adjust the appliance.

A microprocessor 40 can be provided on or embedded within the body plate 12. In order to power the microprocessor, a battery 42 would also be provided. The microprocessor may be supplied via conducting wires with information from the sensors and its output can drive the micro-motors 25, 35, via other conducting wires at least partially embedded in the plastic body 12, in order to automatically keep the contact on the teeth at a preset level. In this way patient errors such as missed, over-zealous or reversed screw-turns are eliminated, and the visits to the dental healthcare provider are reduced to an optimized level. Further, the dental healthcare provider can create a force profile that will lead to a desired outcome for the patient. For example, the vectors need to be intermittent, cyclic, long-acting, low-level and consistent so as not to over do the application of force and produce an inferior result. This profile may be in the form of data or digital codes stored in a memory that is part of the microprocessor. Thus the microprocessor controls the motors based on the profile data and the readings from the sensors.

The plate body 12 does not include the clasps 16, 18, the labial bow 26, and the 3-D axial springs 28 or 29. The body 12 of device 10, except for the overlay 14, is slightly spaced from the patient's tissue, including the palate and mandibular lingual areas. Therefore, the only portion of the plate body 12 that touches the patient's tissues is the overlay 14, which contacts the biting (occlusal) surface of at least one of the patient's teeth in the space where that tooth would normally contact an opposing tooth from the opposite set of teeth, i.e., upper or lower jaw. The overlay 14 is sufficiently thick to prevent the jaws from fully closing. The thickness of the overlay, where it contacts the tooth preferably ranges from approximately about 0.5 mm to approximately about 2 mm. But, the overlay can have a thickness ranging from approximately about 0 mm to approximately about 5.0 mm. The plate body 12 has a thickness that varies and ranges from about 1 mm to about 5 mm.

To change the form of the jaw and facial bones with device 10, the device is placed within the mouth of a patient so that overlay 14 contacts at least one tooth and the remainder of the plate body 12 is spaced from the patient's tissue, including the palate. Overlay 14 prevents the patient's jaws from fully closing. It is believed that this contact of the teeth with the overlay causes intermittent forces to be applied to the body plate 12 and through it to the 3-D axial springs 28, 29 to the teeth. This cyclic intermittent signaling stimulates the patient's genome during function, essentially each time the patient speaks, swallows, smiles etc., which is estimated to be about 2,000 to 3,000 times per day/night. This frequent cyclic intermittent signaling on the facial and alveolar bones is believed to cause development of the facial and jaw bones where jaw development did not fully occur during childhood. This bone development may include a descent of the palate (i.e., remodeling of the vault of the palate downwardly toward the lower jaw); a widening of the palate; an upward and outward remodeling of the body of the maxilla; and an increase in palatal length, if necessary.

FIGS. 7, 10, 12 and 14 show the teeth and mouth of a patient at the beginning of treatment prior to use of the device 10 of the present invention. FIGS. 8, 11, 13 and 15 is the same patient after partial treatment (for one week) of the device 10. It should be noted that the teeth have been re-positioned more favorably in the "after" figures of 8, 11, 13 and 15 when compared to the "before" FIGS. 7, 10, 12, and 14). In effect the jawbone has been developed to accommodate the new position of the teeth. Notice that tooth X and tooth Y are now better aligned because of the effects of the device 10. This alignment was brought about by the application of intermittent cyclic signals to the patient's tissues. During function, e.g., as the patient swallows while wearing the device, either while awake or asleep, the teeth come into contact with the overlay 14, which applies signals through the device to the bones of the jaw. This repetitive signaling causes stimulation of the genes that encode the bones of the jaw and face. While not wishing to be held to any theory of operation, it is believed that the symmetrical nature of the result of the reformation of the teeth and jaw bones is not due entirely to the application of force to specific areas of bone, but to the developmental mechanisms encoded at the genetic level of the patient, as predicted by the Spatial Matrix Hypothesis of Singh.

The vibrational signals from the 3-D axial springs (for example spring 28, 29 of FIGS. 1-6) stimulate the patient's jaw (alveolar) and facial bone genes while wearing the device, which is estimated to be for about 20-30 minutes per day and/or while sleeping at night. This frequent, cyclic, intermittent signaling of the facial and alveolar bones causes development of the facial and jaw bones that did not occur optimally during childhood. This bone development may include remodeling of the palate, eruption of the teeth, remodeling of the facial bones and jaws etc., according to the patient's genome. It should be noted that the teeth are expected to relocate outwards; in effect the jawbone will be expanded to accommodate the new positions of the teeth, without any new spacing occurring between individual teeth.

The spring 28 and 29 is also known as an orthodontic spring and comprises a resilient material. Suitable materials, well-understood in this art, include, for example, a Titanium-Niobium-Aluminum (Ti—Nb—Al) alloy, a Cobalt-Chromium-Nickel alloy, also known under the trade name "Elgiloy®" available from Elgiloy Specialty Alloys of Elgin, Ill., USA, or a NiTi wire that exhibits "super-elasticity".

Additionally, the spring 28 and 29 is further comprised of a wire composed of a single strand of alloy. Alternatively, this spring is constructed from a braided wire composed of a plurality of strands of a single alloy. In yet another embodiment, this spring is constructed from a braided wire composed of a plurality of strands of a plurality of alloys. Other contemplated alloys include a Nickel-free β-titanium alloy.

Further, the spring 28, 29 includes a spring body having an arm 30 and oppositely spaced head 32. The spring body further includes three axes of movement. The three axes include a transverse axis (from side to side across the tooth), an antero-posterior axis (from the front biting edge of the tooth back towards the gum), and a vertical axis (spring loops extending up away from the tooth, and down towards the tongue).

Although the invention has been particularly shown and described with reference to certain embodiments, it will be understood by those skilled in the art that various changes in form and detail may be made without departing from the spirit and scope of the invention.

I claim:

1. An orthopedic-orthodontic appliance for inducing remodeling of craniofacial hard and soft tissues including at least one tooth, the appliance comprising:
   a base plate comprising a first half and a second half, the base plate further comprising at least two overlays adapted to overlay an occlusal surface of posterior teeth bilaterally wherein one overlay is adapted to overlay an occlusal surface of a left-side of a jaw and the second overlay is adapted to overly a second occlusal surface of a right-side of the jaw;
   a contacting material comprising at least one axial spring adapted to contact the palatal/lingual surface of at least one tooth, the contacting material coupled to the base plate, wherein the contacting material is adapted to produce and transmit intermittent, cyclic forces to the palatal/lingual surface of the tooth;
   a midline medio-lateral actuator adapted to permit separation of the first half and the second half, the midline medio-lateral actuator being disposed intermediate therebetween;
   clasps coupled to the base plate, the clasps being adapted to bilaterally contact a posterior of at least one tooth;
   and wherein the at least one axial spring comprises a 3-D axial spring comprising
      a continuous spring body comprising an arm portion at a proximal end and
      a head portion at a distal end, the head portion being adapted to contact the palatal/lingual surface of at least one tooth in an orientation approximately parallel to the long axis of the tooth and anchored by a base-plate
      the head portion comprising at least one first minor sinusoidal-shaped coil extending from the proximal end and having a first axis coincident with a long axis of the axial spring, the head portion further comprising at least one first major sinusoidal-shaped coil extending from the proximal end and having a second axis arranged about 90-degrees from the first axis.

2. The oral appliance of claim 1 wherein the first half and the second half each further comprise a hard acrylic material.

3. The oral appliance of claim 1 wherein the contacting material comprises a wire composed of a single strand of alloy.

4. The oral appliance of claim 1 wherein the contacting material comprises a braided wire composed of a plurality of strands of alloy.

5. The oral appliance of claim 1 wherein the contacting material is orientated at an angle approximately parallel to a long axis of the tooth.

6. The oral appliance of claim 1 wherein the contacting material further comprises a lever arm coupled to a vibrational meso-motor capable of producing intermittent, cyclic signaling.

7. The oral appliance of claim 6 wherein the vibrational meso-motor produces ultrasonic cyclic signaling.

8. The oral appliance of claim 1 wherein the contacting material is adapted to produce intermittent, cyclic forces to the palatal/lingual surface of the tooth whereby such intermitted cyclic forces are produced by intermittent contact of opposing teeth in the maxillary and mandibular dental arches, during swallowing, speech, and mastication.

9. The oral appliance of claim 1 wherein the base plate is made of a self-expanding material.

10. The oral appliance of claim 1 wherein the base plate is made of a hard acrylic material.

11. The appliance of claim 1 wherein the midline medio-lateral actuator further comprises:
    an expansion jack screw being disposed intermediate to, and coupling, the first plate half to the second plate half.

12. The 3-D axial spring of claim 1 wherein:
    the head portion comprises a first minor sinusoidal-shaped coil extending from the proximal end, a second minor sinusoidal-shaped coil disposed adjacent to the first minor sinusoidal-shaped coil and a third minor sinusoidal-shaped coil adjacent to the second minor sinusoidal-shaped coil, each first, second, and third minor sinusoidal-shaped coils being arranged on the first axis coincident with a long axis of the axial spring,
    the head portion further comprising a first major sinusoidal-shaped coil extending from the proximal end, a second major sinusoidal-shaped coil disposed adjacent to the first major sinusoidal-shaped coil and a third major sinusoidal-shaped coil adjacent to the second major sinusoidal-shaped coil, each first, second, and third major sinusoidal-shaped coils being arranged on the second axis, the second axis being disposed about 90-degrees from the first axis.

13. A 3-D axial spring designed for and used within an orthopedic-orthodontic oral appliance inducing physiologic tooth movements in accord with the patient's genome, the spring comprising:
    a continuous spring body comprising an arm portion at a proximal end and a head portion at a distal end, the head portion being adapted to contact the palatal/lingual surface of at least one tooth in an orientation approximately parallel to the long axis of the tooth and anchored by a base-plate;
    the head further comprising three axes of movement, the three axes comprising a transverse axis, an antero-posterior axis, and a vertical axis;
    and wherein the spring body being further adapted to produce and transmit intermittent, cyclic signals to said palatal/lingual surface of said at least one tooth; and wherein
       the head portion comprising at least one first minor sinusoidal-shaped coil extending from the proximal end and having a first axis coincident with a long axis of the axial spring, the head portion further comprising at least one first major sinusoidal-shaped coil extending from the proximal end and having a second axis arranged about 90-degrees from the first axis.

14. The orthodontic spring of claim 13 wherein the spring body comprises a closed coil configuration.

15. The orthodontic spring of claim 13 wherein the spring body comprises a lever arm of a vibrational meso-motor, the spring body being adapted to produce micromechanical and intermittent, cyclic signaling.

16. The orthodontic spring of claim 13 wherein the intermittent, cyclic signals are produced by intermittent contact of opposing teeth in the maxillary and mandibular dental arches, during swallowing, speech and mastication, and other such functional stimuli.

17. The 3-D axial spring of claim 13 wherein:
the head portion comprises a first minor sinusoidal-shaped coil extending from the proximal end, a second minor sinusoidal-shaped coil disposed adjacent to the first minor sinusoidal-shaped coil and a third minor sinusoidal-shaped coil adjacent to the second minor sinusoidal-shaped coil, each first, second, and third minor sinusoidal-shaped coils being arranged on the first axis coincident with a long axis of the axial spring,
the head portion further comprising a first major sinusoidal-shaped coil extending from the proximal end, a second major sinusoidal-shaped coil disposed adjacent to the first major sinusoidal-shaped coil and a third major sinusoidal-shaped coil adjacent to the second major sinusoidal-shaped coil, each first, second, and third major sinusoidal-shaped coils being arranged on the second axis, the second axis being disposed about 90-degrees from the first axis.

18. A method for achieving concurrent craniofacial correction of a patient, the method comprising:
providing an orthodontic appliance having a means for providing micromechanical and cyclic forces, the means comprising at least one 3-D axial spring coupled to the appliance, and wherein the at least one 3-D axial spring comprises
a continuous spring body comprising an arm portion at a proximal end and
a head portion at a distal end, the head portion being adapted to contact the palatal/lingual surface of at least one tooth in an orientation approximately parallel to the long axis of the tooth and anchored by a base-plate
the head portion comprising at least one first minor sinusoidal-shaped coil extending from the proximal end and having a first axis coincident with a long axis of the axial spring, the head portion further comprising at least one first major sinusoidal-shaped coil extending from the proximal end and having a second axis arranged about 90-degrees from the first axis;
adjusting the appliance to achieve intimate contact with the tissue, including the teeth, but without the use of force that push or pull on the teeth; and
inducing a cyclic stimulus.

19. The method of claim 18 further comprising:
wearing the appliance only at night.

* * * * *